United States Patent [19]
Le Boeuf

[11] Patent Number: 6,099,492
[45] Date of Patent: *Aug. 8, 2000

[54] ELECTRONIC APPARATUS FOR BLOOD TRANSFUSION

[76] Inventor: Guy Le Boeuf, Le Bourg, 86800 Lavoux, France

[*] Notice: This patent issued on a continued prosecution application filed under 37 CFR 1.53(d), and is subject to the twenty year patent term provisions of 35 U.S.C. 154(a)(2).

[21] Appl. No.: 09/066,648

[22] Filed: Apr. 27, 1998

Related U.S. Application Data

[62] Continuation-in-part of application No. 08/691,824, Aug. 5, 1996, abandoned, which is a continuation of application No. 08/244,630, filed as application No. PCT/FR92/01098, Nov. 25, 1992, abandoned.

[30] Foreign Application Priority Data

Mar. 12, 1991 [FR] France .................................. 91 14940

[51] Int. Cl.$^7$ .................................................. A61M 37/00
[52] U.S. Cl. .......................... 604/4; 604/7; 128/DIG. 12; 128/DIG. 13; 222/103
[58] Field of Search ........................... 604/4–7; 222/103; 128/DIG. 12, DIG. 13

[56] References Cited

U.S. PATENT DOCUMENTS

| | | |
|---|---|---|
| 3,565,292 | 2/1971 | Jinotti . |
| 3,625,401 | 12/1971 | Terry . |
| 3,902,635 | 9/1975 | Jinotti . |
| 4,613,327 | 9/1986 | Tegrarian et al. . |
| 4,626,243 | 12/1986 | Singh et al. . |
| 4,657,160 | 4/1987 | Woods et al. . |
| 4,747,826 | 5/1988 | Sassano . |
| 4,874,359 | 10/1989 | White et al. . |
| 5,163,909 | 11/1992 | Stewart ..................... 604/140 |
| 5,328,477 | 7/1994 | Sitko ....................... 604/134 |
| 5,496,303 | 3/1996 | Antonetti ................. 604/410 |
| 5,507,737 | 4/1996 | Palmskog ............... 604/891.1 |

FOREIGN PATENT DOCUMENTS

WO 88/07384  10/1988  WIPO .

*Primary Examiner*—John G. Weiss
*Assistant Examiner*—Dennis Ruhl
*Attorney, Agent, or Firm*—Young & Thompson

[57] ABSTRACT

A blood transfusion device has at least one blood accelerating pump, a variable volume reservoir, at least one single-use blood supply bag, a platen, a blood reheater, a single-use blood reheater bag, a filtration system and a perfusion line. The variable volume reservoir varies in volume using an accordion-like bellows or a flexible pocket acted upon by the blood accelerating pump. The single-use blood supply bag contains concentrated corpuscles, plasma, or a solution of albumin. The blood supply bag is disposed between two plates precisely spaced apart. The platen is acted upon by the accordion-like bellows or the flexible pocket to slide in parallel to the two plates, and is disposed between the variable volume reservoir and the blood supply bag. The blood reheater includes an assembly of two double plates, each double plate having a preheating plate heated to a constant temperature slightly less than 38°, and a heating plate heated to a variable volume controlled by a temperature detector at an outlet of the blood transfusion apparatus. The single-use blood reheater bag is disposed between each of the two double plates and communicates, via an inlet member, with the single-use blood supply bag. The filtration system is disposed at an outlet of the blood transfusion apparatus, and the perfusion line is connected to an outlet of the filtration system by conical couplings, and is terminated in a trocar.

4 Claims, 12 Drawing Sheets

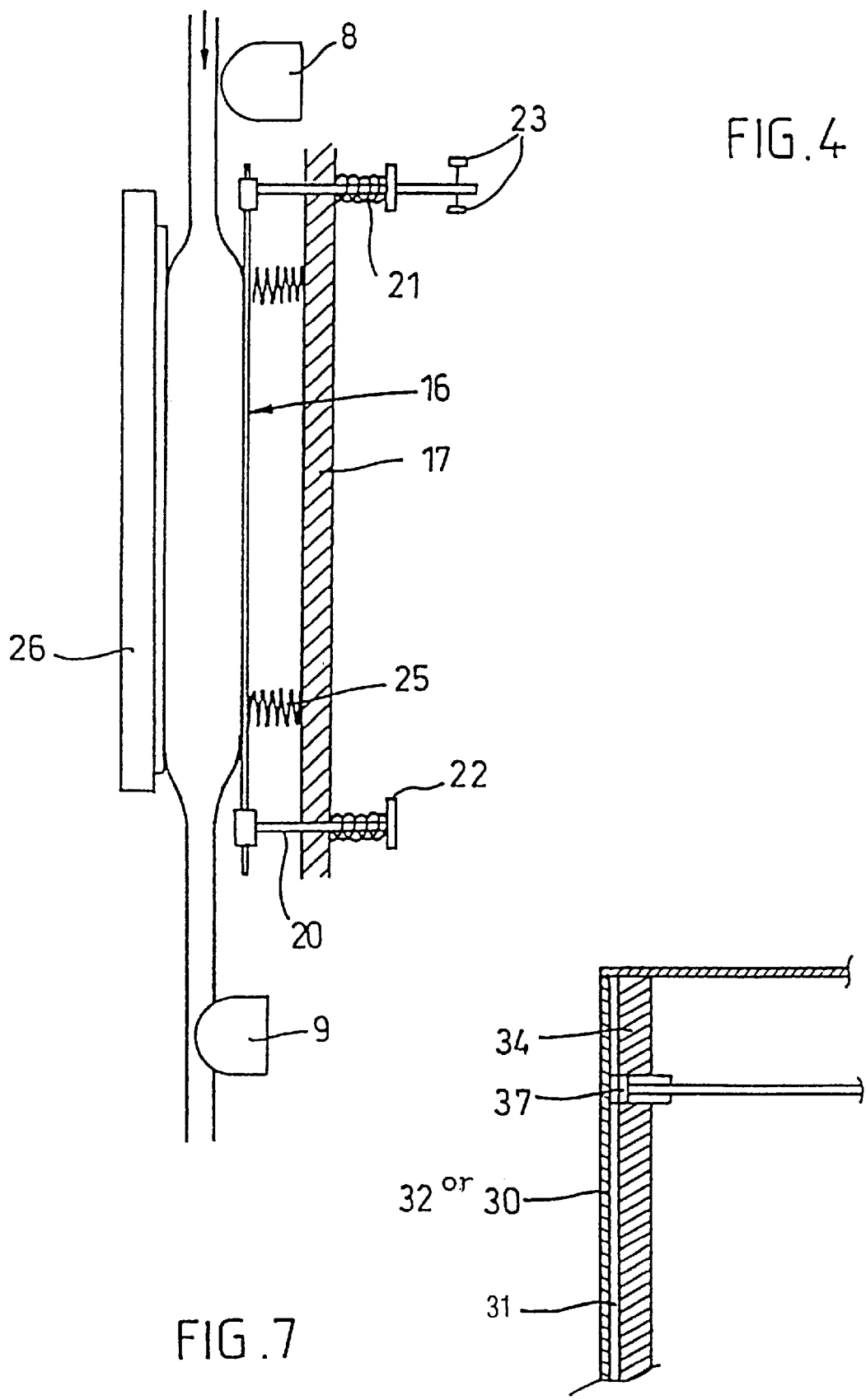

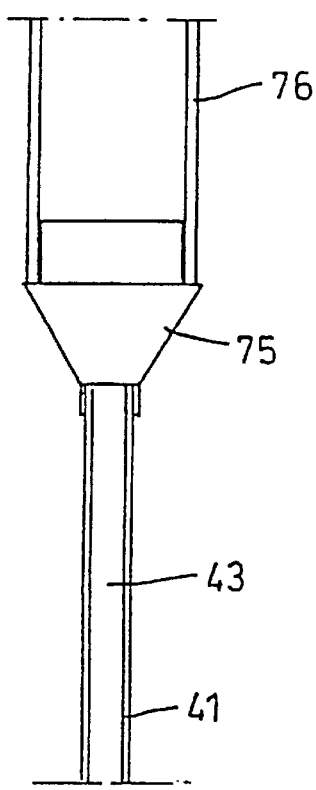
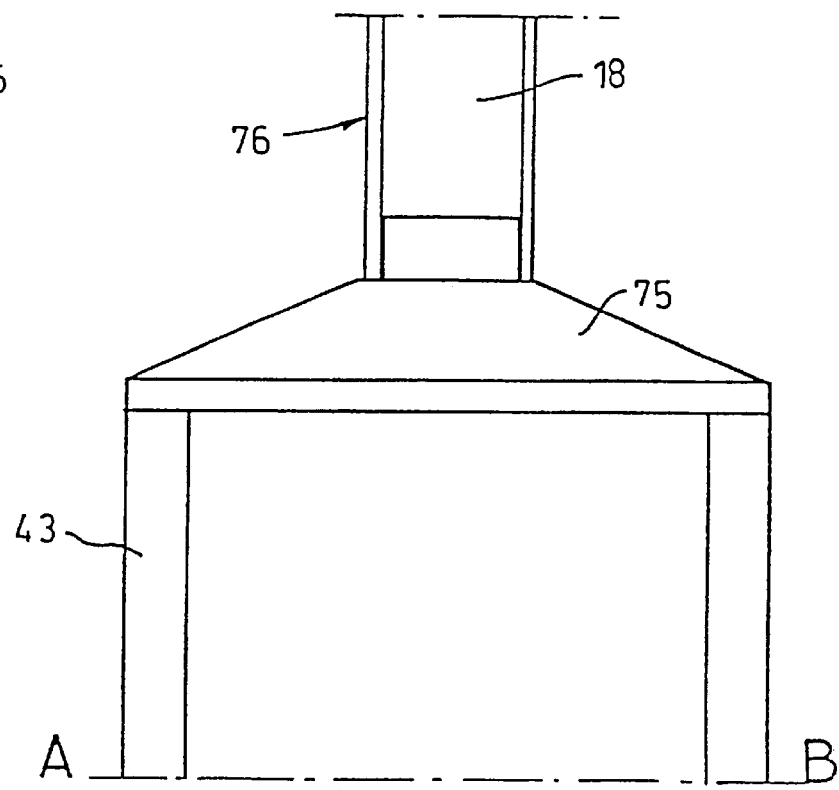
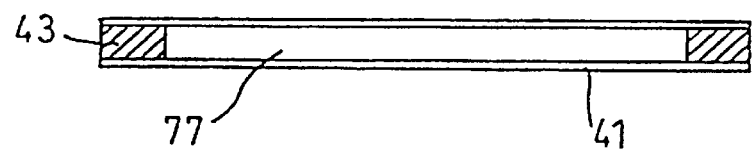
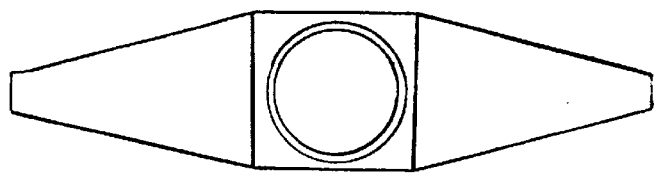

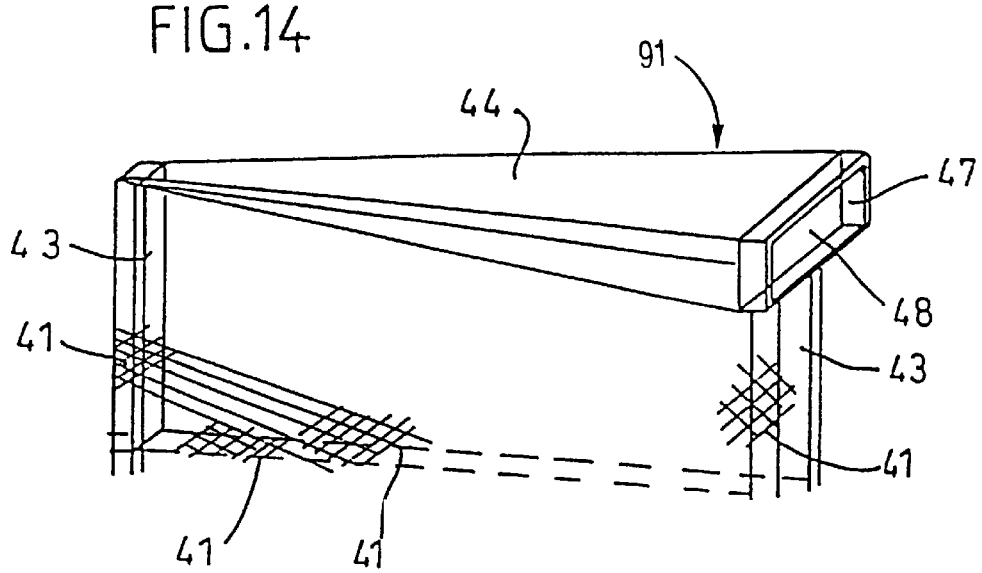
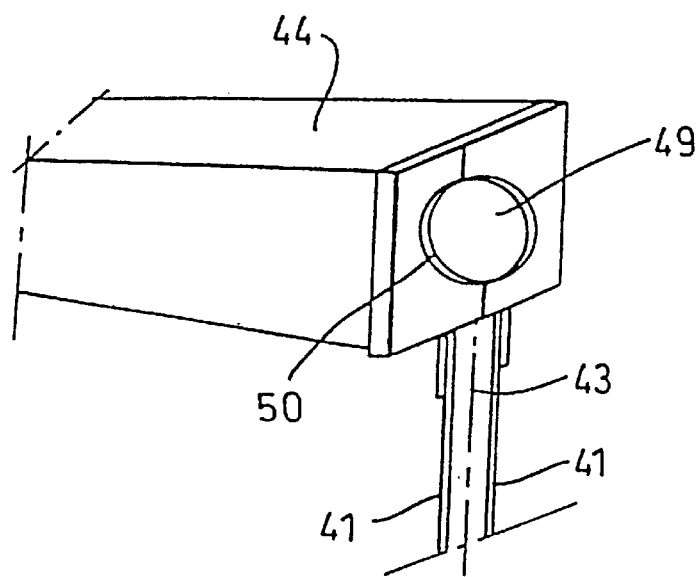
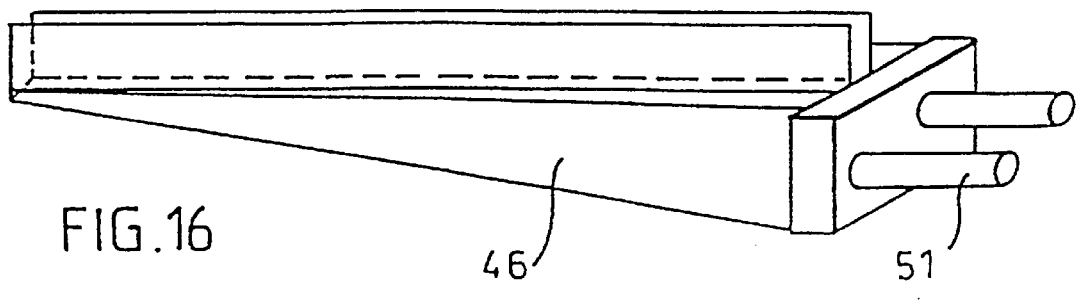

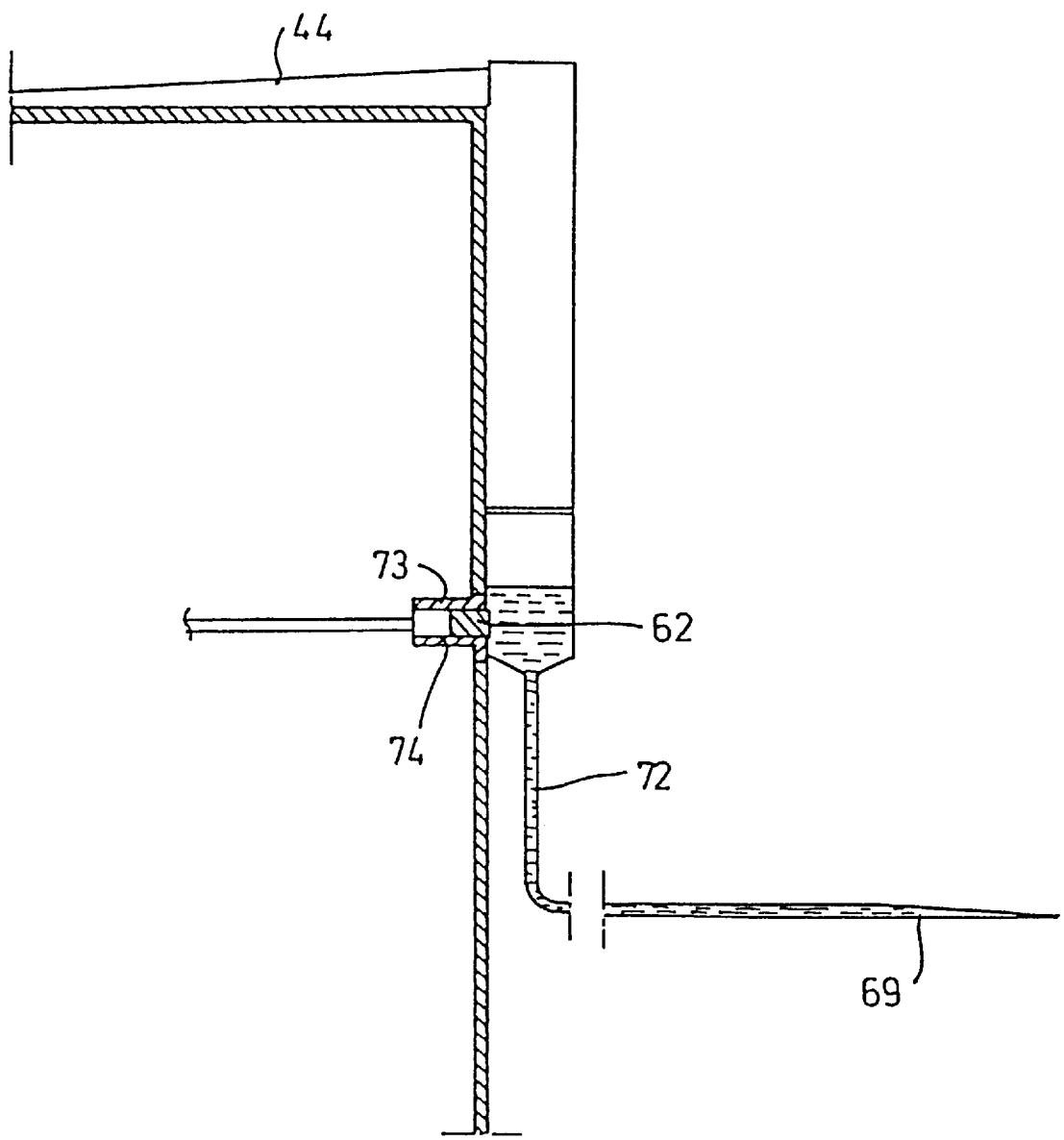

ELECTRONIC APPARATUS FOR BLOOD TRANSFUSION

CROSS-REFERENCE TO RELATED APPLICATIONS

This application is a continuation in part of application Ser. No. 08/691,824, filed Aug. 5, 1996 now abandoned, which is a file wrapper continuation of Ser. No. 08/244,630, filed Aug. 1, 1994 now abandoned, which was the 35 U.S.C. § 371 national phase of International application PCT/FR92/01098, filed Nov. 25, 1992, which designates the United States.

BACKGROUND OF THE INVENTION

From the beginning of blood transfusions, their technique has been improved. First of all there was the preservation of blood in sterile bags of about 300 $cm^3$ at a temperature of +4° C.

For several years, the transfusion centers have separated red corpuscles from plasma, which permits transfusing only the useful part of the blood, either the concentrated red corpuscles (erythrocytes) or the plasma or serum. Apparatus to assist in the transfusion are also known, namely:

1/ pumps for accelerating the blood, to treat as rapidly as possible a hemorrhage which, when it is massive, can lead to death. These pumps of the peristaltic type in the first instance manual have been subsequently controlled by an electric motor of variable speed, electronically controlled.

2/ blood reheaters: doctors have noted that massive transfusions of cold blood lead to about 8% mortality, which is avoided with blood reheated to 37° C. Moreover, clinical studies have shown that the transfusion with reheated blood decreases the transfused volume by about 30%, which decreases the risks of infection (AIDS, Hepatitis B, etc.) and is more comfortable for the patient who is no loner chilled after the procedure.

3/ on the other hand, stored blood contains microaggregates and impurities which it is desirable to eliminate (because they obstruct the superficial blood vessels). In addition to the conventional filter of 173 microns, so-called micro-filters of 40 microns are used.

At present, a transfusion line therefore comprises:

1/ a bag of concentrated red corpuscles, (alternatively a bag of plasma or of solution), 2/ a 175 micron filter, 3/ a 40 micron micro-filter, 4/ a pump for accelerating the blood, 5/ a blood reheater, 6/ a single-use tube for the pump, 7/ a single-use bag for the blood reheater (so-called blood bag) and, 8/ a perfusion line connecting the assembly coupled by conical couplings of the Luer type and a trocar introduced into the vein of the patient.

The application of these different elements is long and the connection of them can sometimes lead to air leaking in, which it is absolutely necessary to eliminate because an introduction into the veins of several cubic centimeters of air is fatal.

On the other hand, all the materials occupy a large space adjacent the operating table which must be kept clear as much as possible.

All the present pumps used are of the peristaltic type, namely, conventional, with a retrograde flow during abrupt inflation of the outlet tubing at the time of disengagement of the roller, or without retrograde flow.

The pumps which have a retrograde flow require an electronic detector of the presence of air which stops the pump in case of air intake. With continuous flow pumps, having a flow rate which is always in the same direction, air bubbles can be trapped in an apparatus called an air bubble trap, which is not possible in the case of retrograde flow (or alternating flow) because the air traps then fill with air which mixes with the blood under the influence of retrograde flow during each resumed supply of the transfused liquid.

Moreover, the pump and the reheater each have adjustment and monitoring instruments as well as safety devices and alarms (luminous and sonic).

SUMMARY OF THE INVENTION

The present invention has for its object the provision of a compact transfusion apparatus comprising:

1/ a first pump and pump bag of new design to transfuse the concentrated red corpuscles (or whole blood).

2/ a second identical pump and pump bag for the transfusion of plasma, of solution, of albumin or whole blood.

3/ a blood reheater reheating the mixed liquids from the two pumps.

4/ a micro-filter with an air trap.

5/ a single-use transfusion line comprising: two inlet tubes (one for the concentrate and one for the plasma, the solution, the albumin or the whole blood) with Luer cones, a heating bag being dedicated to the blood reheater, the micro-filter, the air trap, a Luer cone and a trocar at the end of the perfusion tube.

All these components are grouped in a single compact apparatus so as to improve the safety of the patients (fewer possibilities for air leaking in) and to simplify setup. This apparatus could be in conventional rectangular shape or of any shape such that it can be centered about the plasma support and rest on a special support so as to improve the stability of the assembly.

In the present apparatus, all the instruments for starting, adjustment and monitoring (outlet temperature of the blood, flow rates of the pumps, transfused volume, alarms) are grouped on a single control panel. Thus, the progress of the transfusion will be easy for the anesthetist to monitor.

BRIEF DESCRIPTION OF THE DRAWINGS

The invention will be better understood from a reading of the following description given with reference to the accompanying drawings, in which:

FIG. 4 is a cross-section view of a portion of the pump of FIG. 3, for a modified embodiment;

FIG. 7 is a cross-sectional view of a detail of the reheating portion;

FIG. 10 is a fragmentary front view of a heating bag according to a different embodiment;

FIG. 11 is a side view of the heating bag assembly of FIG. 10;

FIG. 12 is a cross-sectional view of the heating bag assembly of FIG. 10;

FIG. 13 is a top view of the heating bag of FIGS. 10–12;

FIG. 14 is a perspective view of the upper portion of the heating bag sealed on its frame;

FIG. 15 is a perspective view of a different embodiment of the upper part shown in FIG. 14;

FIG. 16 is a perspective view of the lower part of the heating bag sealed on its frame;

FIG. 17 is a schematic cross-sectional view of a portion of the base of the filter;

DESCRIPTION OF THE PREFERRED EMBODIMENT

There will now be described the various components of the apparatus shown in FIG. 1.

The two pumps used are not of the peristaltic type whose rollers crush the erythrocytes and create a hemolysis of the blood by crushing the red corpuscles (erythrocytes) and hence the deposit in the plasma of a portion of the hemoglobin. A new apparatus is used, which can be called a hydraulic compressive transfer pump.

Figure 3:
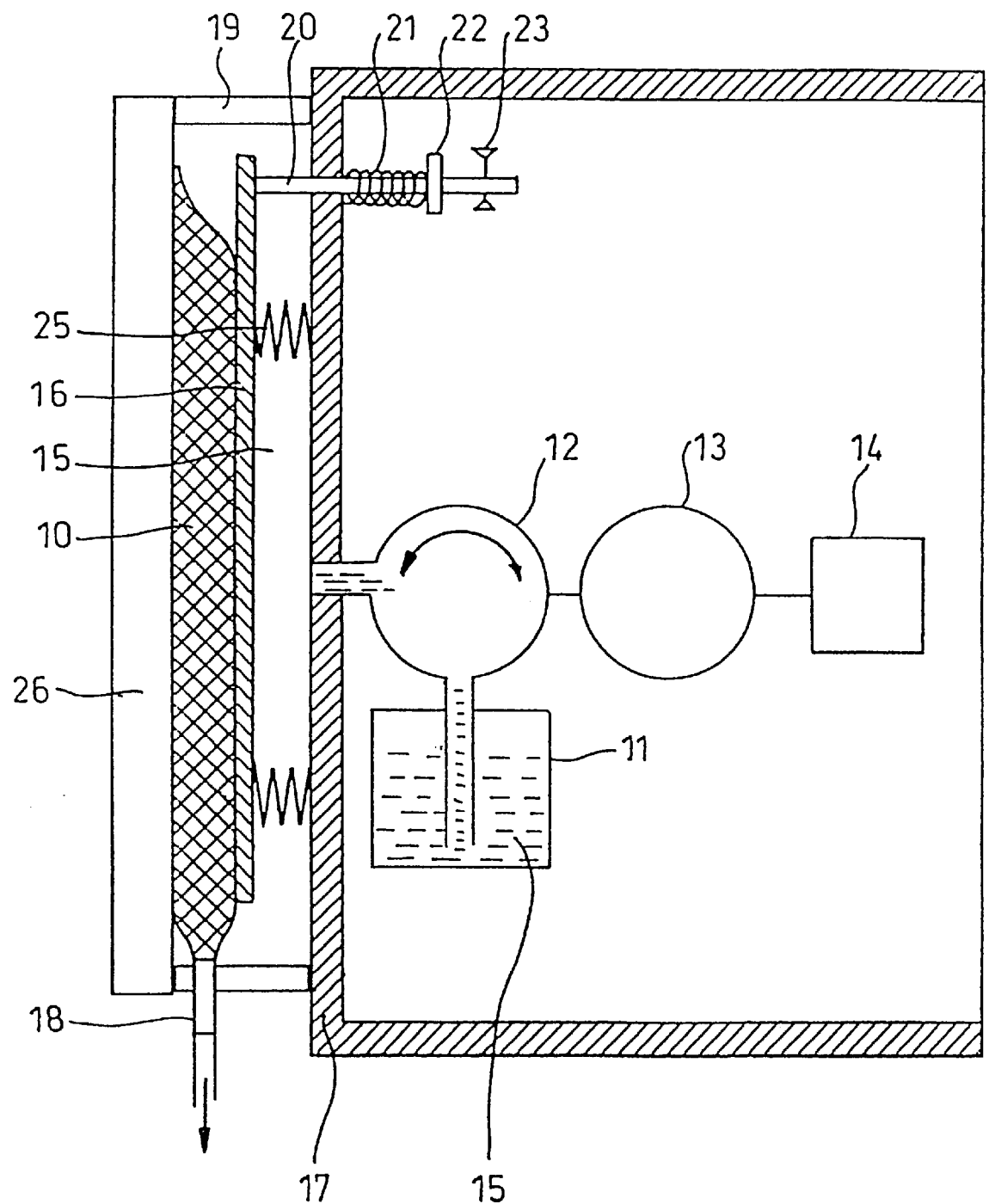
FIG. 3 is a schematic cross-sectional view showing only one pump of the apparatus according to the invention.

This apparatus comprises (for each of the two pumps) (FIG. 3):

a reservoir 11 filled with incompressible transfer liquid 15, for example water, a rotary or peristaltic pump 12 to transfer this incompressible liquid 15 to a variable volume reservoir 25 of the accordion type, an electric motor 13 which actuates the pump 12, an electronic speed controller 14 for the motor 13, variable volume reservoir 25 connected to the pump 12 and which progressively fills with the transfer liquid 15, a single-use pump bag 10 holding liquid to be transfused, separated from the reservoir 25 by a pressure plate 16. Pressure plate 16 bears on the inner surface of pump bag 10; the outer surface of pump bag 10 bears against door 26 of the apparatus in its closed position. Door 26, preferably transparent, has a substantial thickness on the order of 8–10 mm so as not to deform under the pressure exerted by the transfer liquid 15 in the reservoir 25 and to remain in a position strictly parallel to the surface 17 of the housing of the apparatus.

The two pump bags 10 of liquid to be transfused are fixed on the insides of doors 26, which are pivotally mounted on axles 27. When the doors 26 are closed, they are parallel to the surface 17 of the apparatus and the doors are held in place by partitions 19; doors 26 thus are held in a known position and the pump bags 10 filled with liquids to be transfused bear on the deformable compressive reservoir 25 which is of the accordion type (metallic bellows or flexible bag), via a pressure plate 16 which exerts pressure on the pump bag 10.

When the assembly is in place, the motor 13 turns the compression pump 12 which progressively fills the deformable reservoir 25. Reservoir 25 increases in volume and exerts pressure on the pump bags 10 of liquids to be transfused.

The increase of volume of the compression reservoir 25 is proportional to the volume of the liquid transfused and, therefore, to the flow rate of the pump 12. As a result, the flow rate of the transfused liquid is proportional to that of the compression liquid pump and is continuous.

A microprocessor executing a specified program can be used to indicate the instantaneous flow rate of the transfused liquid as well as its volume, which may be displayed numerically on the control panel T of the apparatus and can be transmitted to a computer by an appropriate interface.

The two front doors 26 comprise an automatic stop control of the transfuser when opened, for example by means of a mechanical microswitch or an optoelectronic positive safety system.

In the case of solutions used in a bottle, an empty pump bag 10 may be filled by gravity via a filling inlet. This filling may be assisted by a return to the initial position of the variable volume reservoir 25 from a filled position, thereby creating suction. This return is assisted by a system of springs 21 pressing a pin 20 via its head 22, pin 20 being fixed on pressure plate 16. Pin 20 passes through the surface 17 of the housing which serves as an abutment for the spring 21 to press against the head 22 of the pin 20.

Moreover, at the end of the complete compression of the pump bag 10, the operation of the pump 12 is reversed so as to empty the deformable bellows while transferring the transfer liquid 15 back to the fixed reservoir 11. This control can be effected by an optoelectronic system 23 monitoring the movement of one of the axles 20 (or by a microswitch) according to which the axle intersects or not a light ray (or which mechanically controls the opening and closing of an electric contact).

The pump can be used for extra-corporeal circulation (FIG. 4) using a flow-through pump bag. The blood being introduced as indicated previously, a system of cams 8, 9 alternately closes and opens the inlet and outlet tubes. Upon suction, the inlet cam 8 is opened and the outlet cam 9 closed; conversely, during compression, the inlet cam 8 is closed and the outlet cam 9 is opened to permit evacuation of the blood. The cams 8 and 9 are each controlled by actuators (not shown).

The reheating of the blood or of the red corpuscles concentrate preserved at +4° C. is subject to two requirements:

1/ the temperature should not exceed 43° C. when rising progressively, to avoid hemolysis of the blood (or of the concentrate).

2/ the blood or the red corpuscle concentrate should not be abruptly subjected to a temperature equal to or greater than 38° C. In this case, there is the risk of hemolysis by thermal shock.

Figure 1:
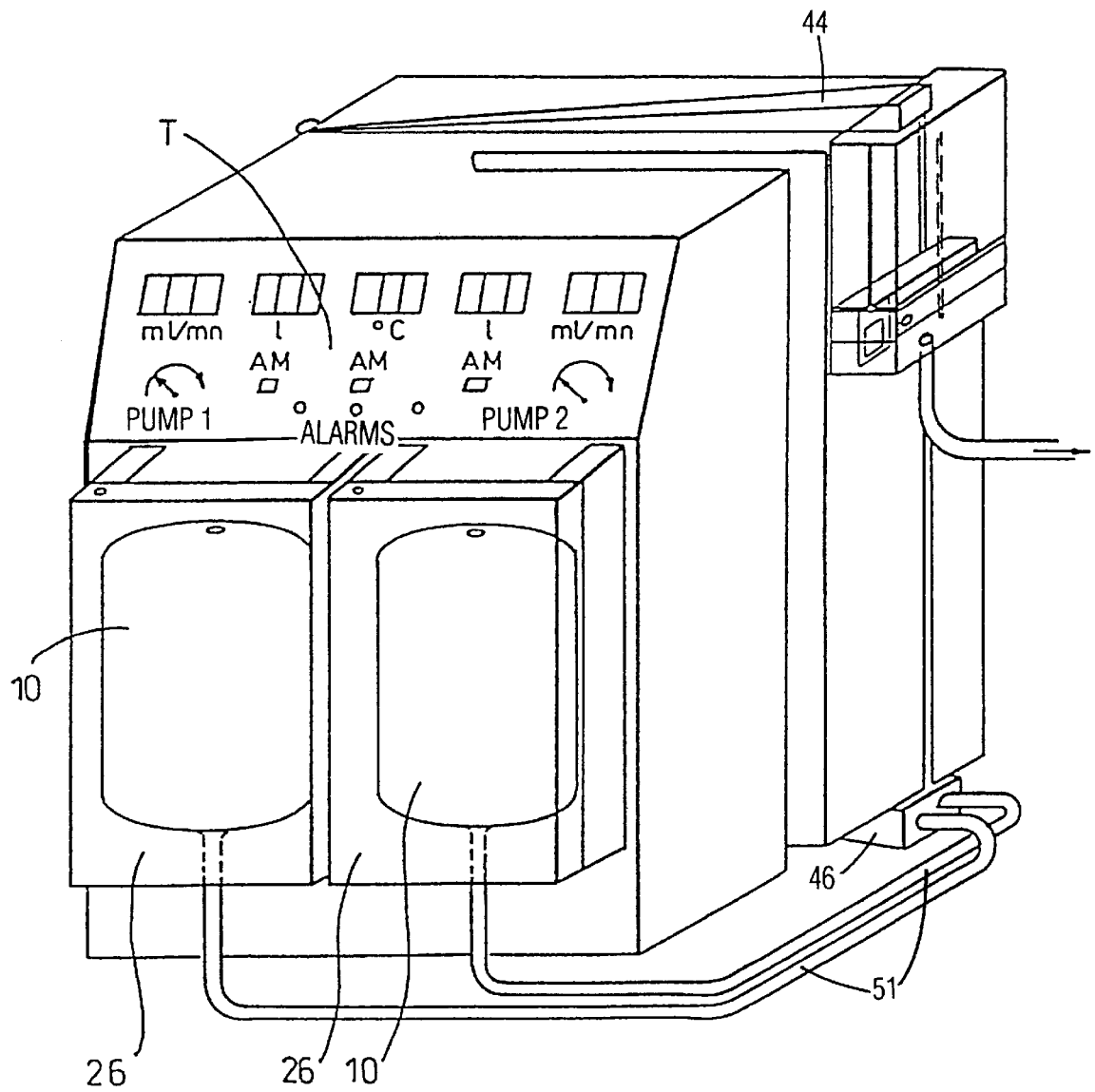
FIG. 1 is a schematic perspective view of transfusion apparatus according to one embodiment of the invention.
Figure 2:
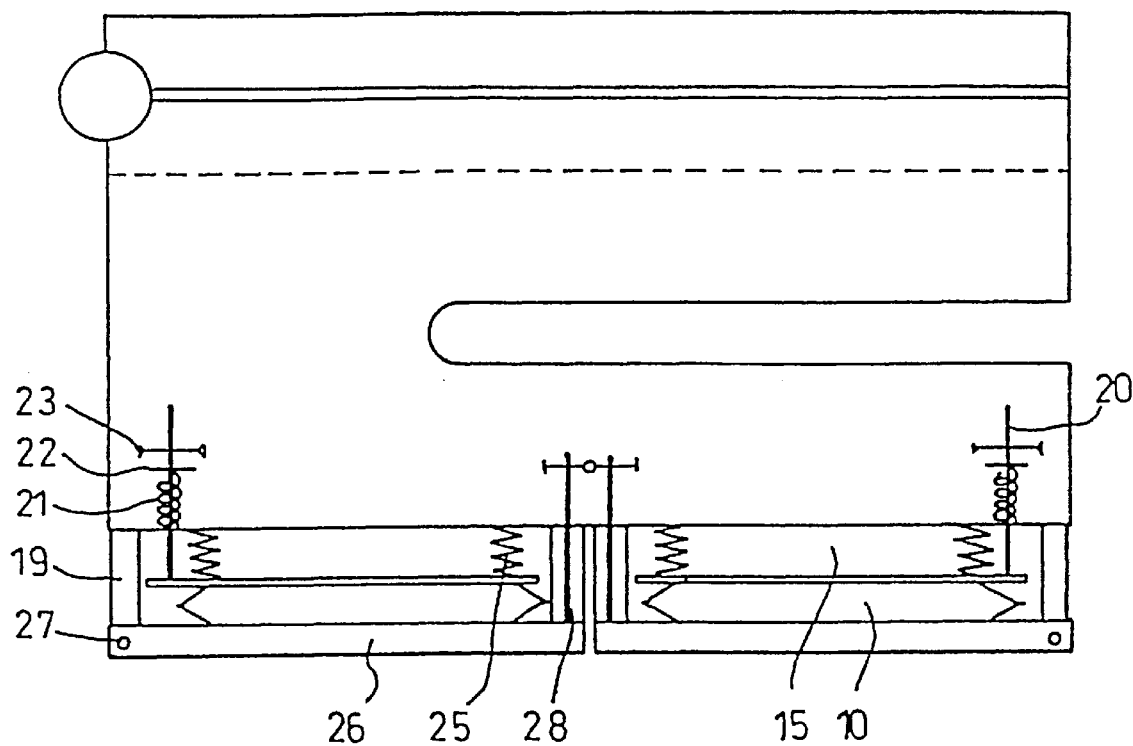
FIG. 2 is a schematic cross-sectional view of the overall apparatus of FIG. 1.
Figures 5, 6:
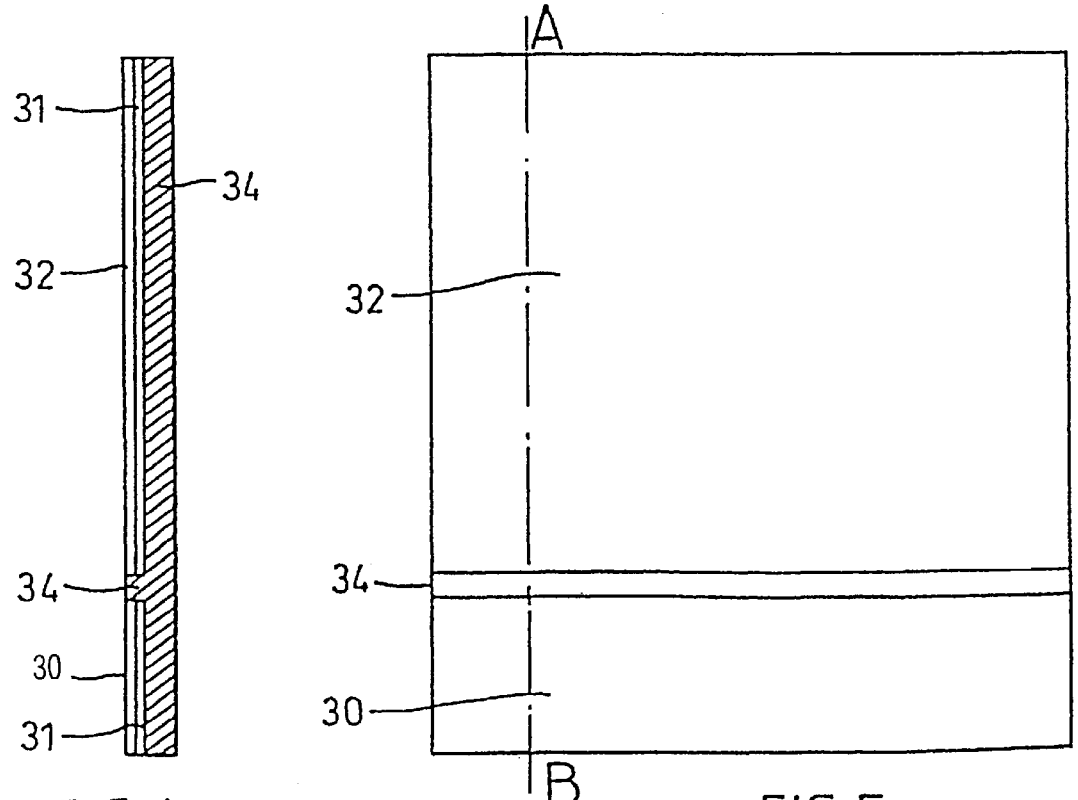
FIG. 5 is a plan view of the preheating and heating plates opposite sides of a heating bag.
FIG. 6 is a cross-sectional view of FIG. 5.
Figure 18:
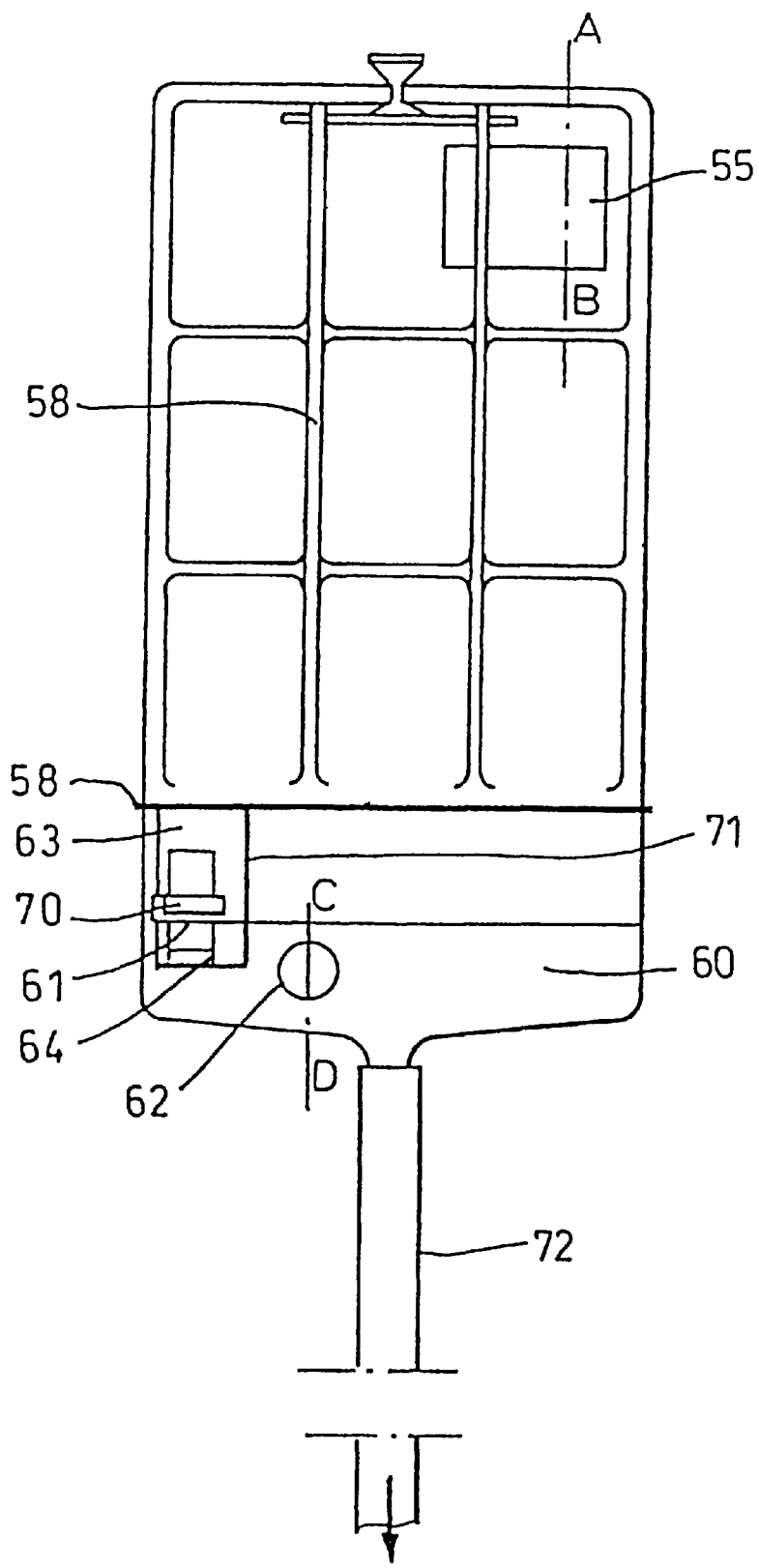
FIG. 18 is a plan view of the filter.

In the apparatus according to the invention, these two requirements are satisfied by a heating system which receives the fluid pumped from pump bags 10 via tubes 51 (FIG. 1). The heating system comprises four plates, two plates being superposed on each side of a single-use heating bag, preheating plates 30 (FIG. 5) disposed below, with a temperature less than 38° C. (for example 36° C.) to avoid hemolysis by thermal shock. The temperature of heating plates 32, thermally insulated from the preheating plates 30 by insulating members 34, is controlled as a function of the outlet temperature of the blood by a temperature detector, located at the outlet of the apparatus on a metallic element 62 (FIGS. 17 and 18) with a safety device preventing exceeding 43° C., the possible hemolysis temperature of the blood. The temperature sensing could also be effected with a metal tube mounted on the tubing, downstream of the filter. The heating container is mounted between the two double plates for preheating and heating so as to increase the output of the apparatus. The heating insulators 31 are mounted in sandwich fashion between the plates 30, 32 and the insulating members 34.

With this system, the outlet temperature of the blood will be, in the perfusion tubing, 37° C. and, at the surface also of the plates, there will be an outlet temperature of 37° C. for a flow rate higher by about 30% because at maximum flow rate the temperature of the preheating plate 30 and of the heating plate 32 will vary from 36°/37° C. at the bottom (preheating plate 30) to 42° C. on the upper heating plate 32 at highest flow rates (instead of 18° C. to 42° C. in a conventional system without preheating).

In the present apparatus, the blood temperature is therefore measured at the metallic element 62 (or tubing) of stainless steel or of metal compatible with blood, which will be directly in contact with the heated fluid, by a detector 73 (FIG. 17, which bears on the metallic element 62 or on the tube fixed to the exterior of the heating bag (on the side of the air trap or on the outlet tubing), which permits an immediate measurement of the heated fluid.

This detector 73 mounted on the side wall and thermally insulated by a member 74 permits indicating directly the temperature of the blood and controls by an electronic assembly (microprocessor), the heating of the upper heating plates 32 according to the principle: Proportional Integral Differential. This therefore implies that this heating plate will be very thin (so as to have a small thermal inertia) such that the blood outlet will be at a temperature of 37.5° C., the ideal temperature for the patient, who always has the tendency to become chilled in the course of the operation, on the one hand by the blood loss and on the other hand by the ambient temperature of the operating room which is on the order of 20° C. A detector 37 (FIG. 7) controls the temperature of the heating plate 32 and halts heating in the case of malfunction (temperature higher than 43° C.). The temperature detector 37 could be, for example, a thermistor or any other conventional detector (such as a thermocouple or resistance). An identical detector measures the temperature of the preheating plate 30 and maintains it, for example, at 36 to 37° C.

In existing apparatus, at the time of high flow rate (greater than 9 liters/hour), the pressure can rise to 1 kg/cm$^2$. Because of this, bags of plastic material of small thickness (0.1 mm to 0.2 mm) often fail either along their lateral edges or at the junction of the outlet or of the inlet of the connection of the tubing with said bag. This follows from the fact that the outlet and inlet sections of the tubing are very much less than the transverse section of the bag comprised between the plates. Another known bag is comprised by a flat tubing of small cross section (about 10 mm$^2$) for high flow rates (9 liters/hour) ; because of its small section, the pressure is very high on the reheating plates and on the lateral sides of the bags.

By contrast, according to the present invention, the pressure on the lateral sides and on the heating plates 30, 32 is very greatly decreased (to the order of 1/20) by an outlet (and inlet) cross section equal to the transverse section of the bag. The advantages are as follows:

1/ no more leakage at the lateral sides,
2/ no more leakage at the connections of the inlet and outlet tubing of the bags, because the pressure of the transfused liquid is low,
3/ the system described therefore permits using this transfuser for much higher flow rates, particularly with extracorporeal circulation, by using the same principle, for flow rates of the order of 200 liters/hour.

Figure 8:
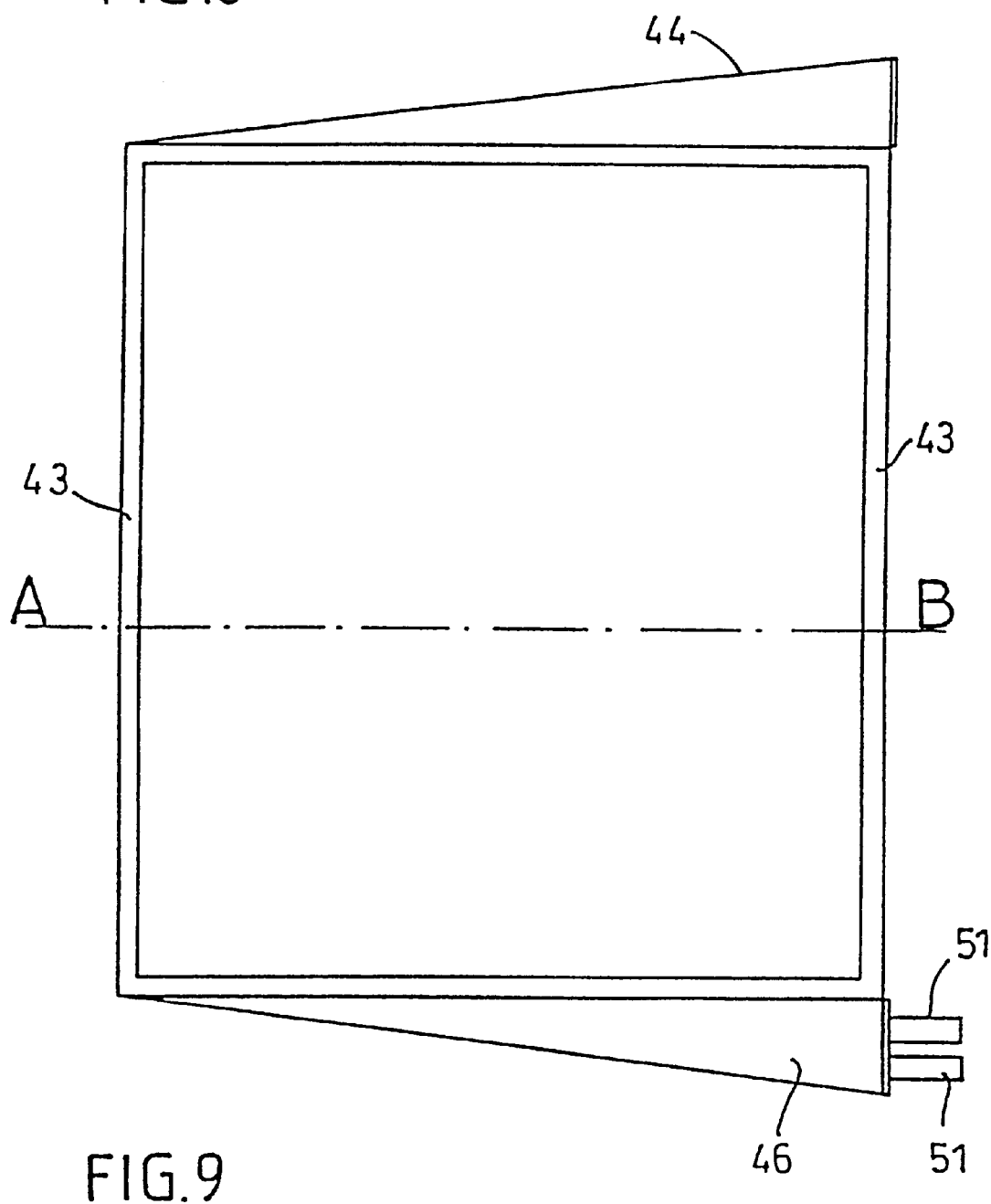
FIG. 8 is a plan view of a heating bag of the reheating portion.
Figure 9:
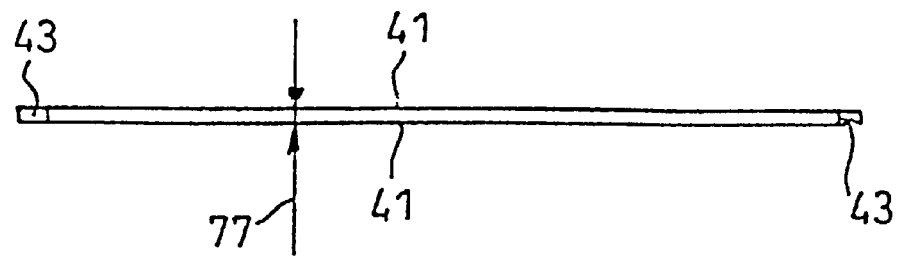
FIG. 9 is a cross-sectional view of FIG. 8.

The single-use heating bag according to the invention is formed simply of two sheets 41 of plastic high-frequency welded together. They comprise laterally a rigid or semi-rigid frame 43 (FIG. 8) of a thickness equal to the spacing between the heating plates (or to this thickness less two times that of the plastic sheets of small thickness 41 of 0.1 to 0.2 mm), such that the sheets 41 are compressed between the frame 43 and the plates 30, 32 whose spacing is very precise and invariable when the apparatus is closed, which is facilitated by the low internal pressure.

The lateral frames 43 comprising partitions between the plates 30, 32 are sealed (or cemented) to the special inlet and outlet members 46 and 91. These latter have an outlet section equal to the transverse section of the heating bag. This is obtained by their special shape (FIGS. 14 to 16). The outlet member 91 (FIG. 14) is sealed to the frames 43 and to the two lateral sheets 41; its upper surface 44 is such that it flares toward the outlet side 48 and ends in a member 47 of square cross section (FIG. 14) or a member 50 with a circular outlet 49 (FIG. 15) and communicating with the filter described above which forms a portion of the disposable portions of the apparatus.

The lower inlet member 46 (FIG. 16) has a cross section of the same size as the outlet member 91. It is sealed to the two lateral sheets 41 and to the frames 43. It has a shape similar to that of the upper member 91. The inlet comprises a member (shaped or molded) having two tubes (FIGS. 16) on which two tubings 51 terminating in a Luer cone are connected to the pump bags of liquid to be transfused.

The inlets and outlets for the fluid can also be axial (see FIGS. 10 to 13), particularly for high flow rates such as those used in extracorporeal circulation. The inlet and outlet members 75 flare from the edges of sheets 41 toward the center to the tubing 76 which has a cross section equal to the transverse cross section 77 of the heating bag comprised between the plates 30 and 32.

Figure 20:
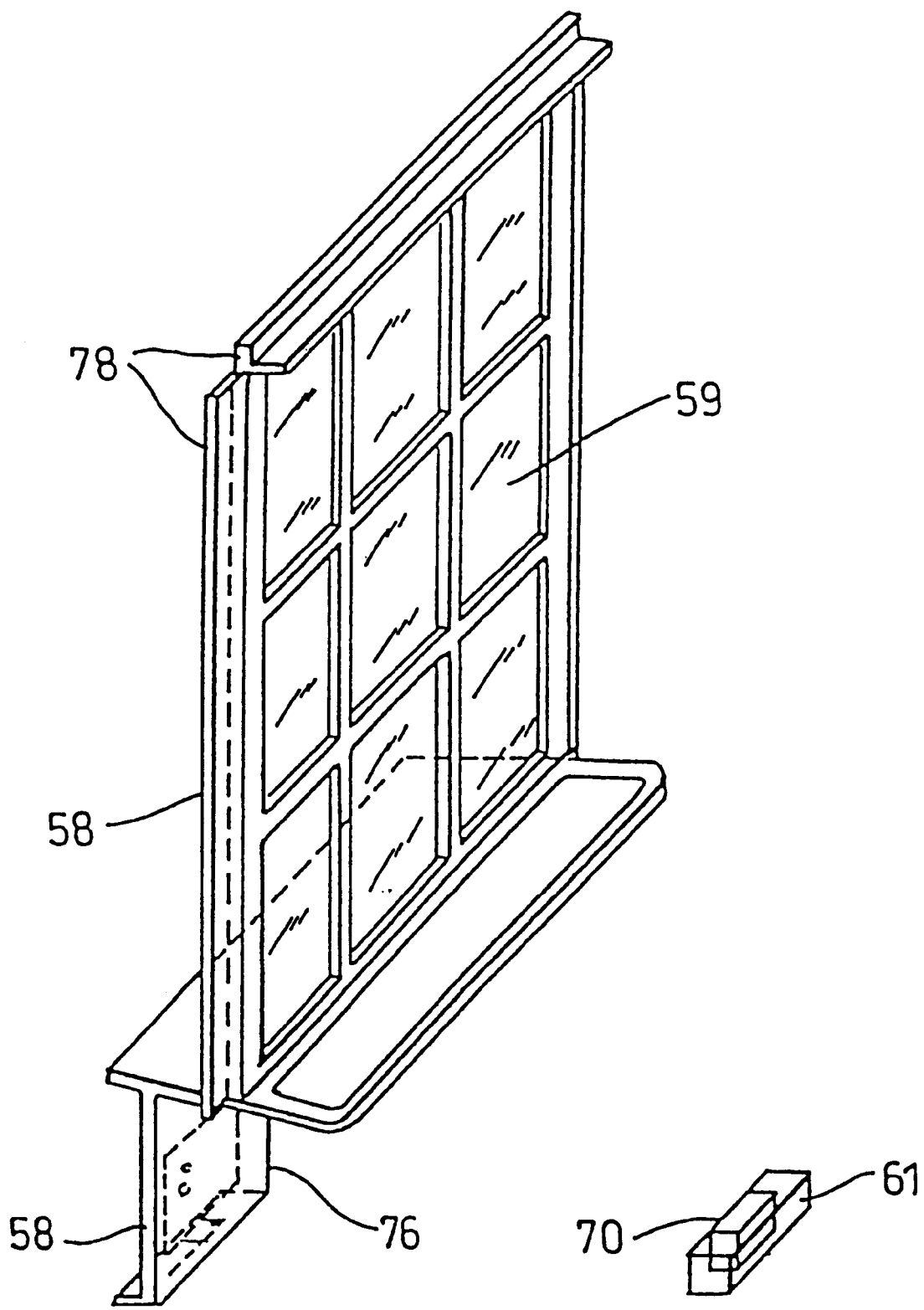
FIG. 20 is a schematic perspective view of the frame of the filter with a micro-filter and a float.
Figure 21:
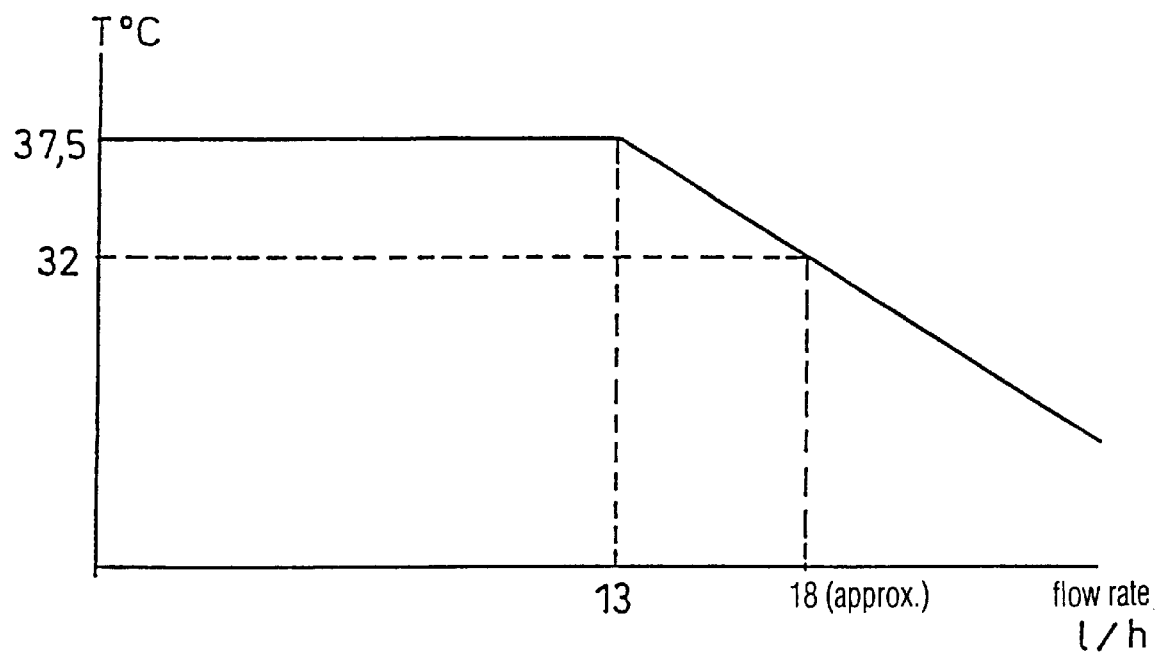
FIG. 21 shows the curve of the outlet temperatures as a function of flow rate.

The filter is of the type described in U.S. Pat. No. 4,320,001 but it comprises the following improvements:

the lower portion is continued after the micro-filter 59 such that the fluid, entering through opening 55 (FIGS. 18–19), after traversing the micro-filter 59 itself, falls into a second volume 60 through an opening in filter frame 58 forming an air trap. In this trap, a float 61 comprising a magnet 70 operates by magnetic control (or by optoelectronic detection) to stop the operation of the transfuser in the case of the two following malfunctions:

1/ upstream constriction of the tubing: in this case, the fluid rises in the trap and the float stops in the upper portion 63.
2/ if for any reason, air is introduced instead of liquid, the float will position itself in the internal portion 64 of the air trap. It is guided by the walls 71 (FIG. 18) and 76 (FIG. 20).

Figure 22:
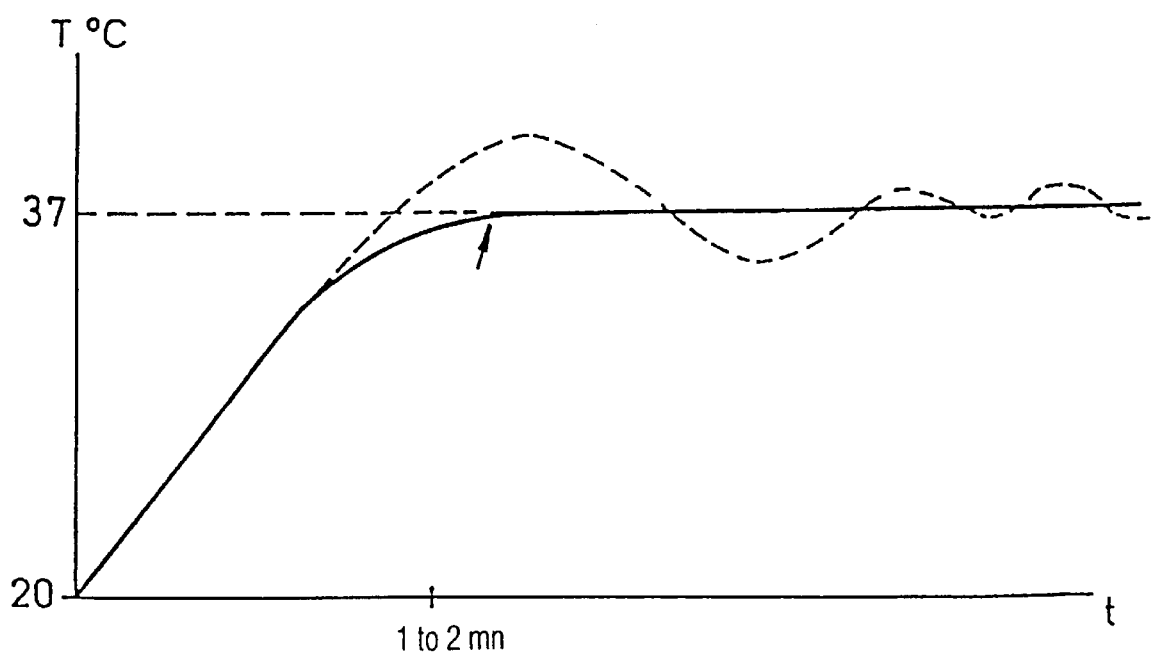
FIG. 22 is a curve showing temperature as a function of time.

On the side of the air trap is secured a metal element of small thickness 62 (FIGS. 18 and 19) for example 0.5 mm, of stainless steel in the perforated wall 52 (or any other heat conductive product which is compatible with blood). As a normal function of the apparatus, metal element 62 will be heated by the blood which is in the base of the air trap on the one hand and will bear on the other hand against a temperature detector 73 (FIG. 17) (thermistor, resistance or thermocouple) which controls and adjusts the temperature of the heating plates 32 between 37° C. and 42° C. such that the blood at the outlet of the filter will be at a temperature of 37° C. in the provided utilization region. The regulation system is conventional (microprocessor) but of the regulation type: proportional, integral and differential, which permits a regular curve without excess temperature (FIG. 22).

The connection of this filter to the upper portion of the heating bag is effected by the outlet element 47 of the heating bag which is received in the opening 55 of the filter. The outlet of the filter is connected by a conventional tubing 72 of about 1.20 meter and terminates in the perfusion trocar 69 (FIG. 19).

Figure 19:
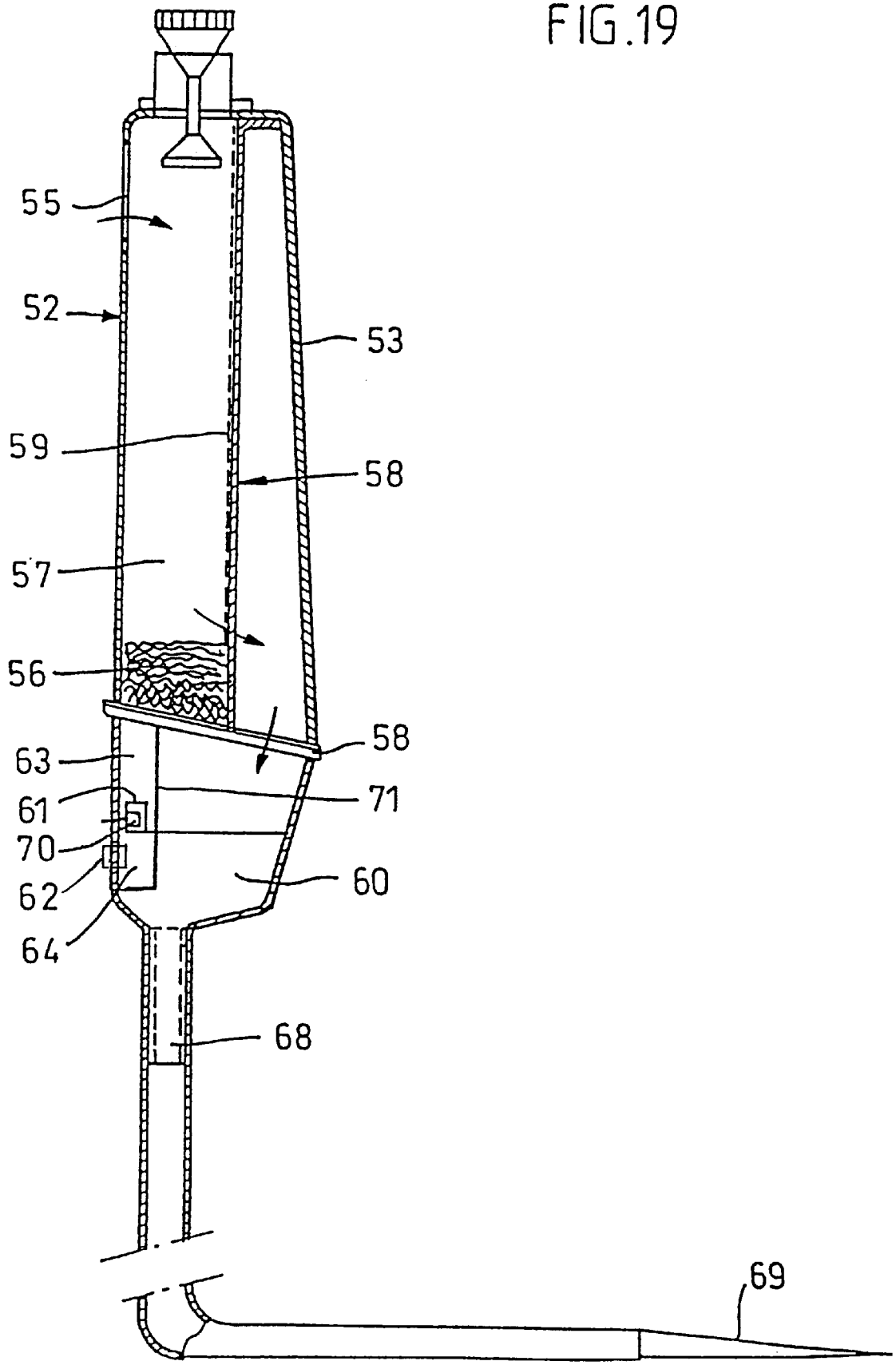
FIG. 19 is a vertical cross-sectional view of the assembly of FIG. 18, showing more detail than FIG. 17.

FIG. 19 also illustrates two interconnected frustoconical elements at the top of the drawing. These elements represent a gas valve assembly disclosed in the above-referenced U.S. Pat. No. 4,320,001. These elements are not required for operaton of the present invention.

What is claimed is:

1. Blood transfusion apparatus comprising:
    at least one compression pump comprising a pump outlet;
    a reservoir of variable volume which varies in volume by means of an accordion-like bellows acted upon by said at least one compression pump, said reservoir being connected to said pump outlet;
    at least one single-use blood supply bag for containing one of concentrated corpuscles, plasma and a solution of albumin, said at least one blood supply bag comprising an outlet and being disposed between two surfaces precisely spaced apart;
    a pressure plate pushed or retracted by said accordion-like bellows so as to remain parallel to said two surfaces, said pressure plate being disposed between said variable volume reservoir and said at least one blood supply bag;
    a blood reheater comprising an assembly of two double plates, each double plate comprising a preheating plate heated to a constant temperature slightly less than 38° C., and a heating plate heated to a variable temperature controlled by a temperature detector;
    a single use blood reheater bag disposed between each of said two double plates, said single use blood reheater bag communicating, via an inlet member, with said at least one single use blood supply bag outlet;
    a filtration system having an inlet and an outlet, said inlet being disposed at an outlet of said blood reheater bag, said filtration system further comprising the temperature detector; and
    a perfusion line connected to said outlet of said filtration system by conical couplings and terminated in a trocar.

2. Apparatus according to claim 1, wherein a cross-sectional area of the outlet of the single-use reheater bag is equal to a transverse cross-section (77) of said single-use reheater bag, said single-use reheater bag also comprising a frame (43) forming a partition having a thickness essentially the same as a distance between said double plates and to which are sealed sheets (41) of small thickness.

3. Apparatus according to claim 1, wherein said filtration system comprises a micro-filtration screen, and is prolonged by an air trap comprising a float (61) and a detection means to detect a position of said float (61) and to control a stopping of said transfusion apparatus in a case of malfunction.

4. Apparatus according to claim 3, wherein a member (62) transmitting heat is fixed in a flat wall of said filtration system bearing on said temperature detector (73) to permit measuring an outlet temperature of said one of concentration corpuscles, plasma and solution of albumin and to adjust said blood reheater.

* * * * *